United States Patent [19]

Pinchuk

[11] Patent Number: 4,629,458
[45] Date of Patent: Dec. 16, 1986

[54] REINFORCING STRUCTURE FOR CARDIOVASCULAR GRAFT

[75] Inventor: Leonard Pinchuk, Miami, Fla.

[73] Assignee: Cordis Corporation, Miami, Fla.

[21] Appl. No.: 705,782

[22] Filed: Feb. 26, 1985

[51] Int. Cl.⁴ .............................................. A61F 2/06
[52] U.S. Cl. ......................................... 623/1; 623/66
[58] Field of Search ............... 3/1.4, 1.7; 273/DIG. 7; 623/1, 3, 66

[56] References Cited

U.S. PATENT DOCUMENTS

| | | | |
|---|---|---|---|
| Re. 31,618 | 7/1984 | Mano et al. | 3/1.4 |
| 3,105,492 | 10/1958 | Jeckel | 623/1 X |
| 3,108,357 | 10/1963 | Liebig | 623/1 |
| 3,166,688 | 1/1965 | Rowand et al. | 623/1 X |
| 3,304,557 | 2/1967 | Polansky | 623/1 |
| 3,425,418 | 2/1969 | Chvapil et al. | 3/1.4 X |
| 3,514,791 | 6/1970 | Sparks | 623/1 |
| 3,562,820 | 2/1971 | Braun | 3/1.4 |
| 3,587,586 | 6/1971 | Kronenthal | 623/66 X |
| 3,625,198 | 12/1971 | Sparks | 3/1.4 X |
| 3,827,426 | 8/1974 | Page et al. | 3/1.7 X |
| 3,921,674 | 11/1975 | Logan et al. | 273/DIG. 7 X |
| 4,044,404 | 8/1977 | Martin et al. | 3/1.4 X |
| 4,047,252 | 9/1977 | Liebig et al. | 623/1 |
| 4,082,893 | 4/1978 | Okita | 623/66 X |
| 4,084,266 | 4/1978 | Poirier et al. | 623/66 |
| 4,167,045 | 9/1979 | Sawyer | 623/1 |
| 4,191,218 | 3/1980 | Chark et al. | 623/1 X |
| 4,313,231 | 2/1982 | Koyamada | 3/1.4 |
| 4,319,363 | 3/1982 | Ketharanathan | 3/1.4 |
| 4,323,525 | 4/1982 | Bornat | 623/1 X |
| 4,441,215 | 4/1984 | Kaster | 3/1.4 |
| 4,466,139 | 8/1984 | Ketharanathan | 3/1.4 |

Primary Examiner—Richard J. Apley
Assistant Examiner—Alan W. Cannon
Attorney, Agent, or Firm—Henry W. Collins; Thomas R. Vigil

[57] ABSTRACT

The reinforced tubular graft structure is particularly adapted for cardiovascular use and is made of collagenous tissue with a reinforcing fibrous structure surrounding the lumen. The fibrous structure comprises a coiled monofilament which can have a textured surface defined by randomly disposed strands of polymer on the outer surface of the monofilament. The coil can be embedded within the collagen or positioned about the collagen to form the graft structure.

42 Claims, 9 Drawing Figures

REINFORCING STRUCTURE FOR CARDIOVASCULAR GRAFT

BACKGROUND OF THE INVENTION

1. Field of the Invention

The present invention relates to a reinforcing structure for use with cardiovascular grafts. More particularly, the invention relates to the provision of a fibrous structure in the form of a coiled monofilament which is positioned within a biograft during formation of the biograft or which is coiled around an existing biograft and which becomes part of the biograft when collagen ingrowth takes place therearound.

2. Description of the Prior Art

Heretofore various graft structures which are reinforced against tearing have been proposed.

For example, the Ketharanathan U.S. Pat. No. 4,319,363 discloses a vascular graft or prosthesis which is reinforced with a mesh into which collagen ingrowth takes place.

Also, the Kaster U.S. Pat. No. 4,441,215 discloses a vascular graft made of synthetic material having a braided inner layer and compliant outer covering layer. The braided layer comprises a plurality of interwoven groups of filaments made of plastic or metal with the filaments being joined at the ends of the formed graft by tacking of adjoining filaments.

Further, as disclosed in the Mano, et al. U.S. Pat. No. Re 31,618, a polytetrafluoroethylene graft with reinforcing structure can be formed by winding a coil of elastic fibers therearound and then fixing the fibers around the graft by solvent bonding. Here, since the graft is completely made of synthetic materials, the reinforcing fibers are only positionable on the outside of the graft and cannot be incorporated within the graft structure itself. Fibers can be wrapped closely in contact with one another or at some interval, with the resiliency or radial compliance being determined by the elasticity of the fibers utilized and the solvent bonding thereof to the graft.

Due to the nature of the reinforcing structures proposed in the patents referred to above, grafts formed according to the teachings of those patents are limited with regard to radial compliance, i.e., the ability to increase the internal diameter of the graft. Such ability of increasing internal diameter is very important with regard to minimizing the possibility of thrombosis.

Also, such prior art grafts are limited by kinking. Knitted or woven meshes kink while a spring configuration does not kink.

The graft with reinforcing structure of the present invention provides for radial compliance of the graft structure by providing a loosely wound coil of monofilament either within the wall of the graft structure being formed or by placing the coil around the graft structure and allowing collagen ingrowth to secure the coil to the graft structure. The provision of a wound coil, with a predetermined pitch to the turns of the coil, provides a graft structure where the internal diameter of the structure can vary with flexing of the graft structure. Also, the smaller the angle of pitch, the greater the radial compliance.

SUMMARY OF THE INVENTION

According to the present invention there is provided a reinforced graft particularly adapted for cardiovascular use. The graft comprises a tubular structure having a central lumen and includes collagenous tissue having a generally tubular shape and a single monofilament wound in a coil with spacing between the turns of the coil to permit the tubular structure to be bent without crimping, the turns having "radial compliance", i.e., the turns going from one pitch to another pitch during bending. The monofilament has a smaller single monofilament painted thereon in an overlapping manner to form a textured mesh-type surface with random interstices into which tissue can grow. The coiled monofilament with the textured mesh-type surface thereon is situated externally of the lumen of the tubular structure.

An advantage of the graft of the present invention is the much improved kink resistance of the graft. Current knitted, woven or ovine grafts, with simple mesh reinforcements, tend to kink in flex areas such as knee joints, or when wrapped around the heart as in coronary by-pass grafts. The radius of curvature of these grafts before kinking occurs is approximately 5 inches, while the spring reinforced grafts of the present invention allow for a much smaller radius of curvature (less than 1 inch) and therefore provide better kink resistance than non-spring-reinforced grafts.

Furthermore, the radius of curvature before kinking occurs is determined by the angle of pitch in which the spring is wound; the higher the pitch angle, the better the kink resistance, the worse the radial compliance. A pitch angle of approximately 60 degrees provides for both good kink resistance and good radial compliance.

DESCRIPTION OF THE PREFERRED EMBODIMENT

Figure 1:
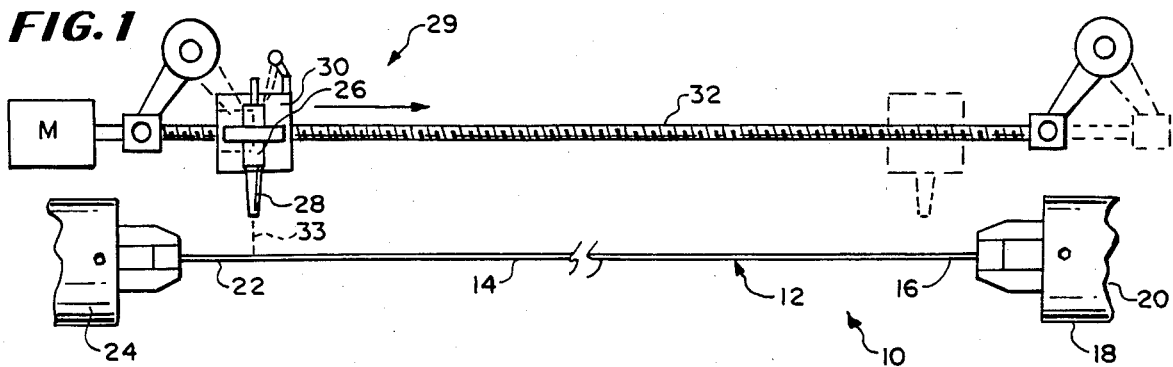
FIG. 1 is a top plan view of a lathe which is utilized to form a reinforcing monofilament according to the teachings of the present invention.

Referring now to FIG. 1 in greater detail, there is illustrated therein a lathe 10 utilized in forming a resilient fibrous-spring like reinforcing structure 12 according to the teachings of the present invention. The structure 12 begins as a ½ mm thick polymeric monofilament 14, one end 16 of which is tied to a drive chuck 18 on a drive end 20 of the lathe 10. The other end 22 of the monofilament 14 is tied to a tail chuck 24. Although a polymer monofilament 14 is preferred, a metal monofilament made of stainless steel, nitrinol or elgiloy can be used instead.

After the monofilament 14 has been secured to the chucks 18 and 24, the tail chuck 24 is positioned so as to apply a slight degree of tension to the monofilament 14.

Next, the monofilament 14 is rotated at approximately 2000 rpm, just below whiplash velocity. The monofilament 14 is rotated by simultaneous rotation of the chucks 18 and 24 of the lathe 10 in the same direction.

As the monofilament 14 is rotated, the surface can be textured by "painting" a polymer thereon.

A syringe 26 with a 27-gauge needle 28 forms a "painting" assembly. This assembly 29 contains a polymer therein and is mounted on a slidable fixture or platform 30. The platform 30 rides on a track 32 and the track 32 is positioned for movement parallel to the axis of the monofilament 14 and in such a manner as to allow the painting assembly 29 to travel the track and "paint" the exterior surface of the rotating monofilament 14. In the use of the 27-gauge needle 28, a fluid stream or strand 33 exiting the needle 28 upon actuation of the assembly 29 can be caused to have a diameter of approximately 10–20 microns.

The polymer within the syringe 28 is dissolved in a solvent and the solution is squirted out of the needle 28 in the fluid strand 33 onto the rotating monofilament 14 by appropriate pressure on a syringe plunger of the assembly 29. However, the painting is done in a special manner to provide the monofilament 14 with a particular textured surface.

For this purpose, the monofilament 14 is rotated at approximately 2000 rpm and preferably has a length of approximately 6 feet. Then the assembly 29 on track 30 is moved back and forth, axially, at a rate of approximately 8 inches per second in axial back and forth strokes of 6 inches in length. Further, as the assembly 29 is moving back and forth, the platform 30 is also being moved axially in one direction at a velocity of approximately 10 inches per minute. This movement of both the assembly 29 on the platform 30 and the platform 30 on the track 32 continues until the entire length of the monofilament 14 has been painted with the fluid polymer strand 33.

Figure 3:
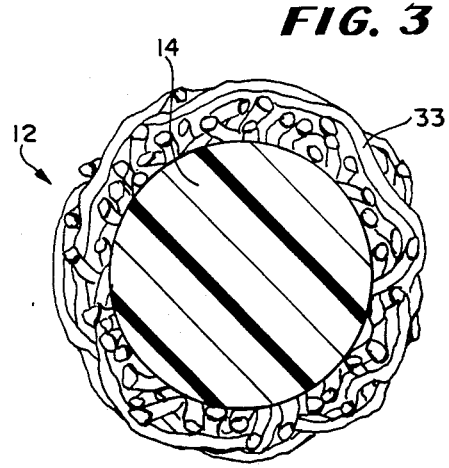
FIG. 3 is a sectional view of the textured surface monofilament of the present invention, is taken along line 3—3 of FIG. 2 and shows fibers of polymer loosely interwoven on the surface of the monofilament to form the textured surface.
Figure 4:
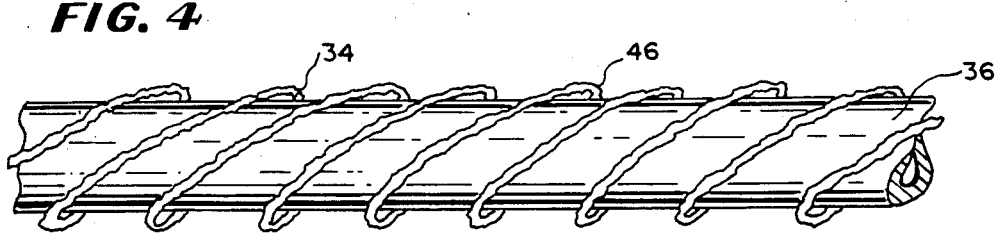
FIG. 4 is a side view of the textured surface monofilament of the present invention wound around a tube which is inserted into a host for the growth of collagen therearound.

By this method of application of "painted" polymer strand 33, a 6 foot long textured surface monofilament having a fibrous external surface as shown in FIGS. 3 and 4 is produced.

Once the textured strand 33 dries, the fibrous monofilament 14 is formed into a coil or spring like structure 34 as shown in FIG. 4 by wrapping the monofilament 14 around a silicone rubber rod or tubing 36 of predetermined diameter, ranging from 2 mm to 3 cm, and having a length of approximately 2 feet.

Figure 5:
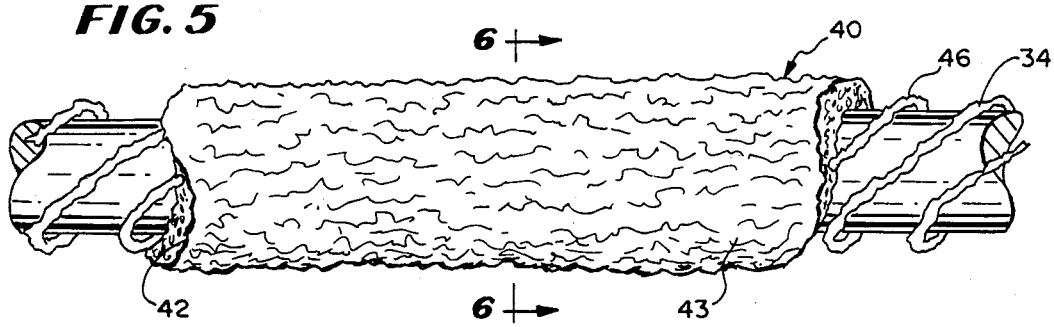
FIG. 5 is a side view of a graft formed with the coiled monofilament positioned therein on the tube with portions broken away.
Figure 6:
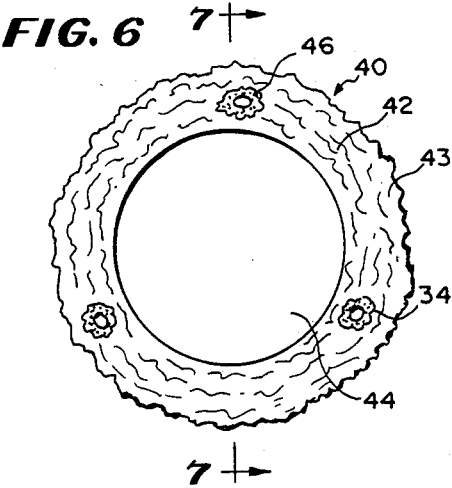
FIG. 6 is a sectional view of the graft shown in FIG. 5 and is taken along line 6—6 of FIG. 5.

Once the coil 34 is formed around the silicone rubber tubing 36, the coil 34 and tubing 36 are placed within a sheep's body and a collagen network attaches itself to the coil 34 forming a reinforced cylindrical graft 40 (FIG. 5). A wall 42 (FIG. 5) of the graft 40 formed in this manner is illustrated in FIG. 6 and will typically have a thickness between 0.5 mm and 0.25 cm and comprises the coil 34 embedded in collagen 43.

Returning to the formation of the coiled filament 14 around the silicone tubing 36, when the coil 34 is being formed, the need for radial compliance must be taken into account. Radial compliance, when dealt with in connection with the formation of a graft structure, is the ability of the graft, e.g., graft 40, to expand its internal diameter when a bolus of blood passes through a lumen 44 thereof. This expandability or radial compliance is provided to the graft structure 40 of the present invention by providing a pitch of approximately 60° to turns 46 of the coil 34 formed from the textured surface monofilament 14 (FIG. 4). Lower pitch angles, such as 45°, give better radial compliance than 60°, however, 60° gives good kink resistance.

By providing the graft 40 with a high degree of kink resistance, it can be utilized in areas having a low flow rate of blood, such as around joints, e.g., at the knee.

The pitch of approximately 60° provided to the turns 46 of the coil 34 provides such radial compliance by providing the graft 40 with the ability to have the pitch of the turns 46 of the coil 34 flex as a bolus of blood passes therethrough. In this respect, by providing a coil 34 that is rather loosely wound (determined by the pitch of the turns 46 of the coil 34) the turns 46 of the coil 34 can expand in diameter due to forces applied to the inside of the coil 34 by flexing away from the center to, in effect, increase the internal diameter of the lumen 44 of the graft 40, in sections.

A graft 40 which does not have a high degree of radial compliance would quickly tear or become thrombosed by large boli of blood passing therethrough and would, in effect, be useless for peripheral vascular anastomoses.

With the coiled monofilament 14 of the present invention, a further step can be added to the formation of the coil 34 to ensure a predetermined diameter of the envelope or cylinder formed by the coil 34 and pitch to the turns 46 of the coil 34. This step can be accomplished by thermosetting of the coil 34 after winding the monofilament 14 around a mandrel (not shown) which has a thread thereon with a desired pitch and which provides a desired distance between turns, and then heating the mandrel and the coil 34 therearound to the crystalline melting point of the polymer utilized in the formation of the monofilament 14, maintaining the melting point temperature for a predetermined period of time and then cooling the mandrel (not shown) and polymer coil 34. Such a crystalline melting point would be, for example, in the case of polyurethane, 125° C. Also, an unthreaded mandrel can be used.

Such a thermally set coil 34 can be utilized in two ways. First, it can be incorporated into a graft 40 as described and illustrated in connection with the description of FIGS. 5–7 below and secondly, it can be utilized to reinforce an existing graft structure as will be described hereinafter in greater detail in connection with the description of FIG. 8.

In certain instances, it is preferable to have a graft 40 which has no reinforcing structure at the points of anastomosis. In such an instance, the coil 34 which has been thermally set would be useful in reinforcing a graft 40 which has already been sutured in or is about to be sutured in place and has no reinforcing structure. The thermally set coil 34 can be placed over such a graft structure in the central portion of the graft structure to provide support against tearing within the central portion while at the same time not interfering with the areas of anastomosis by being positioned only around the central area of the graft structure.

Figure 8:
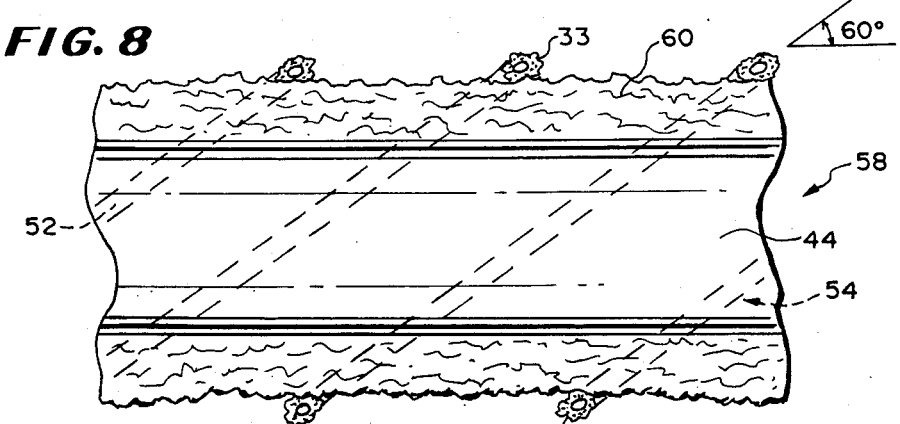
FIG. 8 is a longitudinal sectional view, similar to the view in FIG. 7, of a collagenous shaft having a coiled reinforcing monofilament wound around the graft according to the teachings of the present invention.

Once placed around an existing graft structure 40, as illustrated in FIG. 8, collagen 43 ingrowth from the patient's body will secure the coil 34 to the graft 40.

Figure 9:
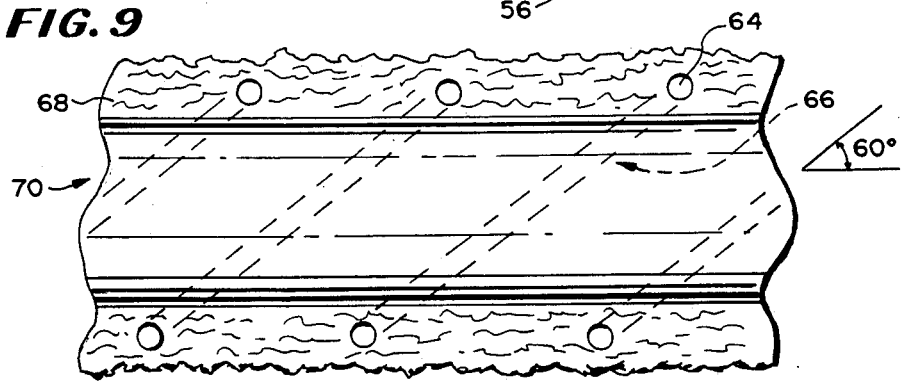
FIG. 9 is a longitudinal sectional view, similar to the view in FIG. 7, of a collagenous graft wall having a plain coiled monofilament positioned therein according to the teachings of the present invention.

Texturing of the surface of the monofilament 14 is provided to establish a network of interstices for establishing deep collagen 43 ingrowth around the coil 34. However, if deep collagen 43 ingrowth is not required, the monofilament 14 can be formed into a coil without "painting" of polymer strands 33 on the monofilament 14. Such a smooth surface monofilament 14 in a coil 48 is illustrated in FIG. 9.

Figure 2:
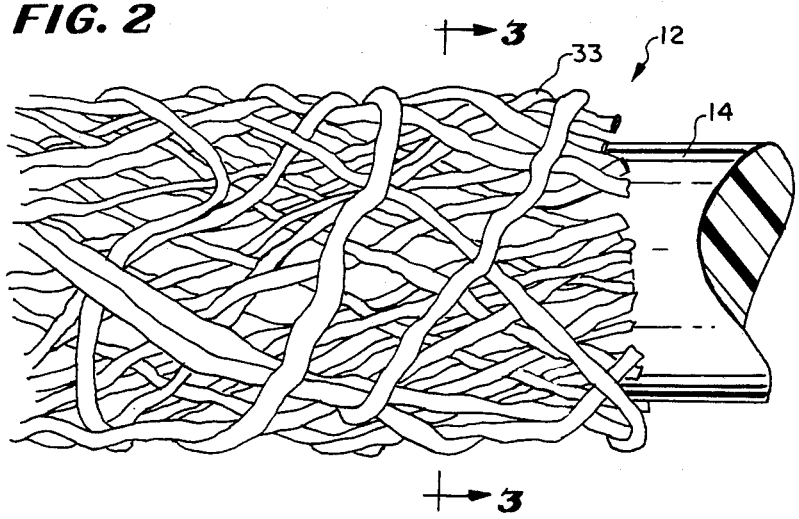
FIG. 2 is a side view of the textured surface monofilament of the present invention.

Referring now to FIG. 2, the monofilament 14 illustrated therein is shown to have a textured surface. As shown, the texturing of the surface of the monofilament 14 is established with a covering, with the fibers or strands 33 being arranged randomly and without pattern. However, because of the unique method of "painting" of the polymer strands 33, it will be seen that the fibers or strands 33 are intertwined adding surface area as well as tensile strength to the monofilament 14.

In FIG. 3, the textured surface monofilament 14 is illustrated in cross section. As shown again, the texturing is provided by the strands 33 on the surface of the monofilament 14 with the strands or fibers 33 being randomly intertwined.

Turning now to FIG. 4, the textured surface monofilament 14 is shown threaded in a coil 34 about a silicone rubber rod 36 prior to insertion of the rod 36 with coil 34 therearound into a sheep for ingrowth of collagen 43 around the coil 34. The coil 34 of monofilament 14 with a textured surface provides greater surface area and a mesh-like arrangement of fibers or strands 33 within which collagen 43 can anchor itself. This ingrowth secures the coil 34 within the graft 40.

In FIG. 5, the ingrowth of collagen 43 about and around the coil 34 on the rod or tubing 36 to form the graft 40 is shown with portions broken away.

Figure 7:
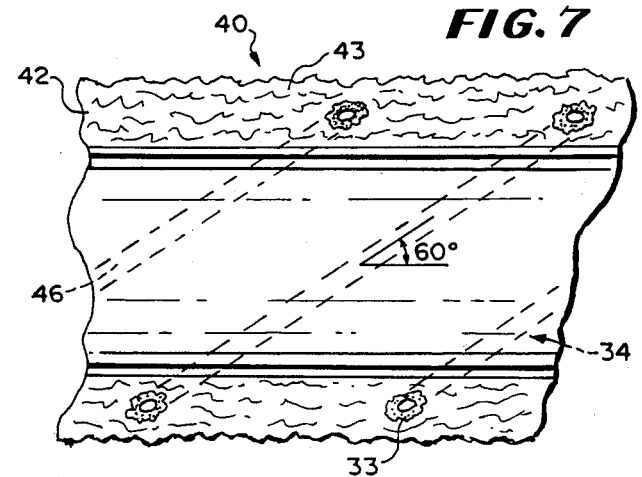
FIG. 7 is a longitudinal sectional view of the graft shown in FIG. 6, is taken along line 7—7 of FIG. 6 and shows the pitch of the textured surface monofilament positioned within the graft.

FIGS. 6 and 7 show sections of the graft 40 after the rod or tube 36 has been removed. Here the collagen 43 is shown surrounding the coil 34 and incorporates the coil 34 within the graft 40 around the lumen 44.

If desired, to provide a graft 40 which has an extra degree of reinforcement, a mesh screen (not shown) may be placed around the rod 36 within the coil 34 before the graft 40 is formed to provide a further reinforcement to the cylindrical wall 42 of the graft 40 and to provide another surface within which the collagen 43 can grow and to which it can attach itself.

Referring now to FIG. 8, turns 52 of a loosely formed coil 54 of monofilament 56 can be positioned about a tubular graft 58 of collagen 60. The turns 52 are spaced apart and have a pitch of approximately 60° to the horizontal. By the provisions of the spaced turns 52 with a 60° pitch as shown, when the graft 58 is in place and has blood flowing therethrough, the turns 52 of the coil 54 can be forced apart and vertically inclined to increase the inner diameter of the graft 58 as described previously.

Further, as shown in FIG. 9, a smooth reinforcing monofilament 64 can be formed into a coil 66 without painting and can be embedded in collagen 68 to form a graft 70.

Also it is to be understood that the coils 54 or 64 can be positioned within the lumen 44 of the collagen cylindrical wall 42 of the graft 58 instead of on the outside thereof as shown in FIG. 8 in which case the growth of collagen around the coil 54 or 64 and between coils thereof will, in time, create a relatively smooth lumen.

The monofilament spring with the textured surface facilitates adherence of a collagenous graft matrix to the spring and prevents a sinus tract from forming along the length of the spring. As a result, a graft with a spring having a textured surface may be preferred over a graft with a plain spring which may not be adhered to the collagenous graft matrix, allowing it to be pulled out of the graft, and also creating a sinus tract which can fill with fluids.

From the foregoing description, it will be apparent that the grafts 40, 58 and 70 with reinforcing coils 34, 54 or 66 therein or thereon of the present invention have a number of advantages, some of which have been described above and others of which are inherent in the invention. Also, modifications can be made to the grafts 40, 58 and 70 without departing from the teachings of the present invention. Accordingly, the scope of the invention is only to be limited as necessitated by the accompanying claims.

I claim:

1. A reinforced graft particularly adapted for cardiovascular use, said graft comprising: a tubular structure having a central lumen and comprising collagenous tissue having a generally tubular shape and a single monofilament wound in a coil with spacing between the turns of the coil to permit the tubular structure to be bent without crimping, the turns having "radial compliance", i.e., the turns going from one pitch to another pitch during bending, and said monofilament having a smaller single monofilament painted thereon in an overlapping manner to form a textured mesh-type surface with random interstices into which tissue can grow, said coiled monofilament being situated externally of said lumen.

2. The graft of claim 1 wherein said coiled monofilament is centrally located within the collagenous tissue.

3. The graft of claim 1 wherein said coiled monofilament surrounds said collagenous tissue.

4. The graft of claim 1 wherein said coiled monofilament is situated about the lumen of said collagenous tissue.

5. The graft of claim 1 wherein said filament is a coiled monofilament.

6. The graft of claim 5 wherein turns said coiled monofilament have a pitch of approximately 60°.

7. The graft of claim 3 wherein said filament is a coiled monofilament.

8. The graft of claim 1 wherein said coiled monofilament has a pitch of approximately 30° to 70°.

9. The graft of claim 1 wherein said fibrous structure is a coiled textured surface monofilament.

10. The graft of claim 1 wherein turns of said coiled monofilament have a pitch of approximately 60°.

11. The graft of claim 1 wherein said coiled monofilament is made of polymeric material.

12. The graft of claim 11 wherein said polymeric material is polyethylene.

13. The graft of claim 11 wherein said polymeric material is polycarbonate.

14. The graft of claim 11 wherein said polymeric material is polyurethane.

15. The graft of claim 11 wherein said polymeric material is polyether sulfone.

16. The graft of claim 11 wherein said polymeric material is polypropylene.

17. The graft of claim 9 wherein said monofilament is coated with a filament of polymeric material to provide said textured surface.

18. The graft of claim 1 wherein said smaller monofilament is applied to the surface of the monofilament by the random intertwining or painting of a smaller monofilament of the polymeric material on said monofilament before coiling thereof.

19. The graft of claim 1 wherein said coiled monofilament is set by thermoforming.

20. The graft of claim 1 wherein said collagenous tissue embeds itself around the coiled monofilament by implantation of the structure within a living host.

21. A reinforced graft particularly adapted for cardiovascular use, said graft comprising a tubular structure having a central lumen and comprising collagenous tissue, a single monofilament wound in a coil with spacing between the turns of the coil to permit the tubular structure to be bent within crimping, the turns having "radial compliance", i.e., the turns going from one pitch to another pitch during bending, and said monofilament having a smaller single monofilament painted thereon in an overlapping manner to form a textured mesh-type surface with random interstices into which tissue can grow, said coiled monofilament being situated externally of said lumen, and a tube of mesh screen disposed within said collagenous tissue and inwardly of said wound monofilament generally coaxial with the axis of the lumen of said tubular structure for further reinforcing the graft.

22. The graft of claim 5 wherein said coiled monofilament is made of metal.

23. The graft of claim 22 wherein said metal is stainless steel.

24. The graft of claim 22 wherein said metal is nitinol.

25. The graft of claim 22 wherein said metal is elgiloy.

26. A reinforced graft particularly adapted for cardiovascular use comprising a tubular structure having a central lumen, said tubular structure being made of collagenous tissue and including in said tubular structure a single monofilament wound in a coil with spacing between the turns of the coil to permit the tubular structure to be bent without crimping, the turns having "radial compliance", i.e., the turns going from one pitch to another pitch during bending, and said monofilament having a smaller single monofilament painted thereon in an overlapping manner to form a textured mesh-type surface with random interstices into which tissue can grow, said coiled monofilament being situated within said collagenous tissue externally of said lumen.

27. The graft of claim 26 wherein said monofilament is coiled in turns having a pitch between approximately 30° and approximately 70°.

28. The graft of claim 26 wherein said monofilament is made of polymeric material.

29. The graft of claim 26 wherein said smaller monofilament is a filament of polymeric material.

30. The graft of claim 29 wherein said smaller monofilament is applied to the surface of said monofilament by random intertwining or painting of said smaller monofilament on the monofilament before coiling thereof.

31. The graft of claim 26 wherein said coiled monofilament is set by thermoforming.

32. A reinforced graft particularly adapted for cardiovascular use comprising a tubular structure having a central lumen, said tubular structure being made of collagenous tissue and including a single monofilament wound in a coil with spacing between the turns of the coil to permit the tubular structure to be bent without crimping, the turns having "radial compliance", i.e., the turns going from one pitch to another pitch during bending, and said monofilament having a smaller single monofilament painted thereon in an overlapping manner to form a textured mesh-type surface with random interstices into which tissue can grow, said coiled monofilament being situated externally of said collagenous tissue.

33. The graft of claim 32 wherein said monofilament is coiled in turns having a pitch between approximately 30° and approximately 70°.

34. The graft of claim 32 wherein said monofilament is made of polymeric material.

35. The graft of claim 32 wherein said monofilament is a filament of polymeric material.

36. The graft of claim 35 wherein said smaller monofilament is applied to the surface of said monofilament by random intertwining or painting of said smaller monofilament on the monofilament.

37. The graft of claim 32 wherein said coil is set by thermoforming.

38. The graft of claim 1 wherein said monofilament is approximately ½ mm thick.

39. The graft of claim 1 wherein said smaller monofilament has a diameter of approximately 1 to 40 microns.

40. The graft of claim 1 having a wall thickness from said lumen to the outer surface of said graft of between 0.05 mm and 0.25 cm.

41. The graft of claim 26 wherein said smaller monofilament has a diameter of approximately 1 to 40 microns.

42. The graft of claim 36 wherein said smaller monofilament has a diameter of approximately 1 to 40 microns.

* * * * *

UNITED STATES PATENT AND TRADEMARK OFFICE
CERTIFICATE OF CORRECTION

PATENT NO. : 4,629,458
DATED : December 16, 1986
INVENTOR(S) : LEONARD PINCHUK

It is certified that error appears in the above-identified patent and that said Letters Patent is hereby corrected as shown below:

Column 7, line 21, "within" should have been --without--.

Signed and Sealed this

Tenth Day of November, 1987

Attest:

DONALD J. QUIGG

Attesting Officer

Commissioner of Patents and Trademarks